United States Patent
De Leij et al.

(10) Patent No.: US 9,320,259 B2
(45) Date of Patent: Apr. 26, 2016

(54) ANTIMICROBIAL MATERIAL

(75) Inventors: Franciscus Antonius Anna Maria De Leij, Surrey (GB); Mina Kalantarzadeh, Surrey (GB); Tony Hutchings, Surrey (GB)

(73) Assignee: UNIVERSITY OF SURREY, Surrey (GB)

( * ) Notice: Subject to any disclaimer, the term of this patent is extended or adjusted under 35 U.S.C. 154(b) by 202 days.

(21) Appl. No.: 13/130,558

(22) PCT Filed: Nov. 12, 2009

(86) PCT No.: PCT/GB2009/051529
§ 371 (c)(1),
(2), (4) Date: Oct. 6, 2011

(87) PCT Pub. No.: WO2010/058198
PCT Pub. Date: May 27, 2010

(65) Prior Publication Data
US 2012/0034289 A1     Feb. 9, 2012

(51) Int. Cl.
*A61K 9/00*     (2006.01)
*A01K 1/015*    (2006.01)
*A01N 65/06*    (2009.01)
*A01N 65/08*    (2009.01)
*A61L 2/23*     (2006.01)

(52) U.S. Cl.
CPC ............. *A01K 1/0155* (2013.01); *A01K 1/0152* (2013.01); *A01N 65/06* (2013.01); *A01N 65/08* (2013.01); *A61L 2/23* (2013.01)

(58) Field of Classification Search
CPC .................................... A01K 1/015
See application file for complete search history.

(56) References Cited

U.S. PATENT DOCUMENTS

| | | | | |
|---|---|---|---|---|
| 3,980,050 | A | * | 9/1976 | Neubauer ............... 119/172 |
| 4,560,527 | A | | 12/1985 | Harke et al. |
| 4,883,663 | A | * | 11/1989 | Leon Leon ............... 424/757 |
| 5,227,163 | A | | 7/1993 | Eini et al. |
| 2005/0100520 | A1 | * | 5/2005 | Hagura et al. ............ 424/65 |

FOREIGN PATENT DOCUMENTS

| | | | |
|---|---|---|---|
| DE | 195 23 320 A1 | 1/1997 | |
| DE | 198 31 288 A1 | 1/2000 | |
| JP | 7 048530 A | 2/1995 | |
| JP | 200395973 A * | 4/2003 | |
| JP | 2007291054 B2 * | 11/2007 | ............ C07G 17/00 |
| WO | WO 0009172 A1 * | 2/2000 | ............ A61L 2/00 |
| WO | WO 02/098439 A1 | 12/2002 | |
| WO | WO 03/028451 A2 | 4/2003 | |

OTHER PUBLICATIONS

100 Mesh (http://en.wikipedia.org/wiki/Mesh_(scale) (downloaded on Oct. 3, 2013)).*
Mimosa tenuiflora poir (http://web.archive.org/web/20080329192757/http://en.wikipedia.org/wiki/Mimosa_tenuiflora (archived on Mar. 29, 2008)).*
Stem (http://en.wikipedia.org/wiki/Bark (downloaded on Oct. 3, 2013)).*
MSDS for Pine Oil, 2005.*
Machine translation of JP200395973A, Jun. 2015.*
International Search Report and Written Opinion from PCT/GB2009/051529 mailed May 3, 2011.

* cited by examiner

*Primary Examiner* — Paul Dickinson
(74) *Attorney, Agent, or Firm* — Knobbe, Martens, Olson & Bear, LLP

(57) ABSTRACT

The invention relates to a method for preparing antimicrobial material. The method comprises heating material comprising wood or bark or material derived therefrom, under conditions sufficient to render the material antimicrobial. The invention also relates to antimicrobial materials prepared by such methods, and to various uses of the antimicrobial materials, for example in reducing microbial activity in animal bedding, such as that which is used in poultry farming.

16 Claims, 6 Drawing Sheets

ANTIMICROBIAL MATERIAL

The present invention relates to methods of preparing antimicrobial materials, and particularly to methods of preparing materials derived from wood or bark, resulting in them exhibiting antimicrobial properties. The invention extends to antimicrobial materials prepared by such methods, and to various uses of the antimicrobial materials, for example in reducing microbial activity in animal bedding, such as that which is used in poultry farming.

A broiler is a chicken raised specifically for meat production. Uric acid is the end product of nitrogen catabolism in birds, such as chickens and turkeys, and it is excreted in the faeces of these birds. As illustrated in FIG. 1, uric acid is converted by micro-organisms to urea, and, as shown in FIG. 2, ultimately into ammonia. Ammonia is toxic at low concentrations, leading to breathing problems and eye irritation in chickens. Accordingly, there is a need for extensive ventilation in a chicken house (as illustrated in FIG. 4a), such as a poultry broiler unit, which can be very expensive.

Furthermore, as shown in FIG. 3, the ammonia derived from the breakdown of urea combines with water to form ammonium hydroxide. Accumulation of ammonium hydroxide in animal bedding raises its pH, thereby making it caustic which can harm the animal. For example, as shown in FIG. 4b, chickens reared on bedding that is rich in ammonium can suffer from 'caustic burns' to their feet and chests, which reduce the quality of the resultant food product. Clearly, prevention of 'caustic burns' caused by ammonium not only improves animal welfare, but will also reduce farmer's losses as a result of better animal growth and higher quality animal products.

Reduction of microbial activity to prevent microbial conversion of uric acid into ammonia and ammonium in animal bedding is currently achieved by keeping the moisture content of the bedding as low as possible. Reports that claim to be effective in this respect use materials that adsorb moisture from the bedding. However, in practice, it is difficult to maintain low moisture levels in the bedding, as high bird stocking densities are often used, and because condensation and liquid spills occur which result in the bedding becoming increasingly wet. This moisture supports microbial activity, which results in the formation of ammonium from the uric acid that is present in the chicken faeces.

Ammonium is converted into ammonia when the pH rises above pH 7, with concentrations of ammonia becoming significant above pH 8. To prevent the bedding material becoming caustic once the uric acid is converted into ammonia, acidic salts, such as alum ($KAl(SO_4)_2 \cdot 12H_2O$) or sodium-bisulphate, may be added to maintain a low pH. However, these compounds do not last, and are costly to the farmer (at an application rate of 100 g/m$^2$, the cost to the farmer is around £600 for a broiler house containing 40,000 chickens). Furthermore, large amounts of aluminium in the resulting litter, creates waste disposal problems due to elevated heavy metal concentrations. As a result, use of such 'acidifying substances' is not common, and ammonia formation in broiler houses is commonplace.

Another problem with animals, such as of chickens, that are reared for their meat, is the risk of food-borne pathogens. It is believed that 80% of chickens that are sold in supermarkets are infected with *Campylobacter*, and that 20% are infected with *Salmonella*. It is thought that these bacteria find their way from the animal house, and in particular the bedding, into the animal itself. It is believed that the cause of these problems is that animal bedding provides a suitable substrate for these bacteria, which includes high temperatures (25-35° C.), high moisture levels and high concentrations of nutrients found in the faeces, and pH values well within the growth range of these bacteria. Accordingly, there is a significant need to reduce the amount of microbial activity within animal bedding to prevent the growth of these pathogens.

Therefore, in a first aspect of the invention, there is provided a method for preparing antimicrobial material comprising wood or bark or material derived therefrom, the method comprising heating material comprising wood or bark or material derived therefrom, under conditions sufficient to render the material antimicrobial.

As described in the Examples, the inventors tested a variety of materials comprising cellulose, hemi-cellulose- and/or lignin for antimicrobial activity, and have found that wood shavings derived from pine wood and bark, as well as from other materials comprising just cellulose (such as filter paper), exhibit surprising antimicrobial properties after moderate heating.

The material that is heated in the method according to the invention may comprise plant material. For example, the material comprising wood or bark may be derived from any hardwood species. Examples of suitable hardwood species that may be used in accordance with the invention include holly (*Ilex* genus), oak (*Quercus* genus), beech (*Fagus* genus), ash (*Fraxinus* genus), maple (*Acer* genus), poplar (*Populus* genus), willow (*Salix* genus), and chestnut (*Castanea* genus), such as sweet chestnut (*Castanea* sativa).

Alternatively, the material comprising wood or bark used in the method of the first aspect may be derived from a softwood species, for example a conifer or a pine tree. Examples of suitable softwoods that may be used in accordance with the invention include pine (*Pinus* genus), spruce (*Picea* genus), cedar (*Cedrus* genus), fir (*Abies* genus), larch (*Larix* genus), douglas-fir (*Pseudotsuga* genus), hemlock (*Conium* genus), cypress (Cupressaceae family), redwood (*Sequoia* genus) and yew (*Taxus* genus). As described in the Examples, the inventor has found that wood and bark derived from pine, and especially Scots Pine, is surprisingly effective at exhibiting antimicrobial activity following the heat-treatment. Hence, in one embodiment, the material may be derived from the Pinaceae family, and preferably the *Pinus* genus, such as *Pinus sylvestris* or *Pinus nigra*.

The material that is heated may be derived from any part of a plant, for example the trunk (i.e. inner core wood, sap wood or outer bark) or the stems (i.e. inner or outer sections) or the branches (inner or outer sections) or the roots (i.e. inner or outer sections). In particular, the inventor has found that materials derived from either the inner wood regions of the plant or the outer bark itself exhibit significantly more antimicrobial properties after heat-treatment than before the heat-treatment. Although the inventors do not wish to be bound by any hypothesis, the antimicrobial effect is not believed to be caused by the essential oils associated with these materials, as most of the oils are believed to be removed as a result of the heating process.

As described in the Examples, the inventors have investigated the antimicrobial properties exhibited by materials comprising wood or bark or materials derived therefrom that have been exposed to a range of different conditions, including various temperatures, and different exposure times. The inventors found that the materials comprising wood or bark that were heated to at least 50° C. or more exhibited surprising antimicrobial properties. Therefore, the material may be exposed to a temperature of at least 50° C., at least 60° C., at least 70° C., at least 80° C., at least 90° C., at least 100° C., at least 110° C., or at least 115° C. The material may be exposed to a temperature of less than 200° C., less than 190° C., less than 180° C., less than 170° C., less than 160° C., less than 150° C., less than 140° C., less than 130° C., or less than 125° C. The material comprising wood or bark may be exposed to a temperature of between 50° C. and 200° C., or between 75° C. and 175° C., or between 100° C. and 150° C., or between 110° C. and 150° C., or between 110° C. and 130° C., or between 115° C. and 125° C., or between 118° C. and 123° C.

The material comprising wood or bark or material derived therefrom may be exposed to the treatment temperature for at least 30 minutes, at least one hour, at least 1.5 hours, at least 2 hours, at least 5 hours, at least 10 hours, at least 15 hours, at least 20 hours, at least 24 hours, at least 30 hours, at least 36 hours, at least 42 hours, or at least 48 hours. As described in Example 2, it was demonstrated that antimicrobial activity increases with increasing exposure time to the treatment temperature. Hence, the material may be exposed to the heat-treatment for at least 54 hours, at least 60 hours, at least 66 hours, at least 72 hours, at least 78 hours, or at least 84 hours, or more.

The inventors have found that materials comprising wood or bark heated for prolonged periods of time (such as about 24-72 hours) at temperatures of between about 100° C. and 200° C., and ideally between about 100° C. and 150° C., results in significant antimicrobial activity being observed. Therefore, the method may comprise heating materials comprising wood or bark or materials derived therefrom at temperatures of between about 100° C. and 200° C., or between 100° C. and 150° C.

The method may comprise an initial step of removing a section of plant material to be treated from a whole plant. The plant may be alive or dead. It is preferred that, before the heating step, the method comprises a step of processing the material comprising wood or bark so that smaller particles of material are formed. The processing step may comprise grinding the material into a powder, or obtaining shavings or preparing a pulp or the like. It will be appreciated that the wood- or bark-derived material will have a particle size distribution characterized by a mean particle size. The processed material may be any size, but since the antimicrobial activity is believed to at least partially result from contact between the heat-treated material and a microbial cell, smaller particles of the material are believed to be more effective as their surface to volume ratio is larger than that of a larger particle.

Particles may therefore be of any size, but particle sizes of less than 2 mm, or less than 1 mm, or less than 0.5 mm may be preferred. The material may have a mean particle size of less than 0.3 mm, or less than 0.1 mm. Alternatively, the material may be elongate, for example presented as shavings that are long and thin to maintain a large surface to volume ratio. In another embodiment, the material may be converted into a pulp from which paper or cardboard may be made.

The method may comprise a step of encasing or holding the material comprising wood or bark (which may have been processed, for example by grinding) in a layer of material, which contains the material as it is exposed to the heat-treatment step. The layer of material may conduct heat. One example of a suitable material which may be used to encase or hold the material as it is heated is a metal, such as aluminium foil, but any material that conducts heat well to the plant-derived material to be treated is suitable. The heat-treatment step may be carried out in an oven, which is capable of heating the wood- or bark-derived material to the required temperature (e.g. about 120° C.) for the required exposure time (e.g. about 48 hours).

The pressure within the oven may be approximately 15 psi (1 bar). Alternatively, the material may be heated, such as by autoclaving, at pressures of up to about 40 psi. The heating step may be carried out anaerobically (i.e. without oxygen) in a closed container, or aerobicically (with oxygen) in an open container.

The conditions described herein (involving exposure temperature, exposure time and pressure) may contribute to activating the wood- and bark-derived material, such that it exhibits antimicrobial properties, which may then be put to a range of different uses.

Hence, in a second aspect of the invention, there is provided antimicrobial material comprising wood or bark or material derived therefrom, obtained, or obtainable, by the method of the first aspect.

Once the material has been exposed to the heat-treatment step, it may then be used in a variety of different antimicrobial applications. The antimicrobial wood- or bark-derived material according to the second aspect may be used to prevent, combat or treat any microbial infection, be it bacterial or fungal.

Hence, in a third aspect, there is provided antimicrobial material according to the second aspect, for use in preventing, combating or treating a microbial infection.

A bacterial infection which may be treated or prevented with the antimicrobial material of the second aspect or in the use of the third aspect may be a Gram-positive or a Gram-negative bacterial infection. Examples of Gram-positive bacteria which the heat-treated material may be used to combat include those in the phylum Firmicutes, which includes *Bacillus* spp., *Clostridium* spp., *Mycobacterium* spp., *Staphylococcus* spp., *Streptococcus* and *Enterococcus* spp. Examples of Gram-negative bacteria which the heat-treated material may be used to combat include Enterobaceriaceae, such as *Salmonella* spp. (such as *Salmonella enterica*), and *E. coli*. *Campylobacter* spp. is another example of a Gram-negative bacterium which may be treated with the antimicrobial material of the second aspect.

The antimicrobial material according to the second aspect may be used as animal bedding, as its antimicrobial properties prevent the growth of pathogens, such as *Salmonella, Campylobacter, Mycobacterium* and *E. coli*, which are all major animal pathogens. Inhibition of a wide variety of microorganisms involved in the conversion of uric acid and urea to ammonia prevents animal beddings becoming caustic.

Hence, in a fourth aspect there is provided animal bedding comprising the antimicrobial material according to the second aspect.

Advantageously, the bedding of the fourth aspect reduces odours, and increases animal welfare. The animal bedding may be used in the animal rearing industry, for example in poultry, such as of chickens, turkeys, ducks, foul or geese, but also as an animal bedding for pigs, cattle, sheep, horses and other animals. Alternatively, the animal bedding may be used in the pet industry, for example for bedding of rabbits, guinea pigs, hamsters, gerbils or caged birds. The bedding of the fourth aspect may also be used for animals used in animal laboratory testing, such as mice, rats or rabbits (e.g. for knockout/nude mice). The bedding may also be used as animal bedding/litter in husbandry of animals in zoos. The bedding may also be used as animal bedding for the transportation of live animals, or for use as animal bedding/litter for egg laying hens, as *Salmonella enteritidis* is known to infect the ovaries of healthy hens and contaminates the eggs before the shells are formed.

Advantageously, the method according to the first aspect results in the heat-treated wood- or bark-derived material according to the second aspect becoming acidic, having a pH below 7.0, 6.5, 6.0, 5.5, 5.0, 4.5, or below 4.0. Low pH prevents the conversion of ammonium into ammonia, which, in animal rearing facilities, increases animal welfare since ammonia is highly toxic, reduces the requirement and subsequent costs of constant ventilation, allows farmers to comply with IPPC regulations and reduces environmental damage. The antimicrobial material of the second aspect and hence, the bedding of the fourth aspect, has been found to retain its antimicrobial properties at elevated moisture levels, and the antimicrobial material does not require the addition of supplementary compounds required for pH control, which can be costly. Furthermore, to the farmer, the antimicrobial material produced by the method of the invention is almost indistinguishable from materials (such as dried pine shavings) that would normally be used as animal bedding.

The antimicrobial material according to the second aspect may also be used in horticulture to prevent crop losses from plant diseases caused by fungal or bacterial infections. Hence, the material may be used as mulch, i.e. a protective cover over soil that prevents soil-borne pathogens from infecting plants, fruits or vegetables.

Hence, in a fifth aspect, there is provided a mulch comprising the antimicrobial material according to the second aspect.

The mulch according to the fifth aspect may be used to minimise or prevent loss of crops due to microbial infection. For example, 50% of strawberries and 20-40% of grapes are lost to fungal infections, such as *Botrytis*, and 70% of the monetary value of apples can be lost to apple scab. It is believed that such crop losses may be avoided by using the mulch of the fifth aspect. Similarly, after fruit has been harvested, crop losses due to fungal and bacterial infections are common, and it is estimated that post harvest losses at least equal pre-harvest losses. Hence, there is a significant need for antimicrobial materials which can be used in the food packaging industry.

Hence, in a sixth aspect, there is provided a food packaging material comprising the antimicrobial material according to the second aspect.

The food packaging material of the sixth aspect may prevent losses to fresh harvested food products, such as fruits and vegetables, which are susceptible to infection by spoilage organisms, such as fungi and bacteria. To prevent losses caused by these spoilage organisms, the food product may be stored in contact with different forms of the antimicrobial material of the second aspect. For example, the antimicrobial material may be processed in to paper (for example by initially forming a pulp from which paper may be made), which may be used for wrapping the food product. Alternatively, the antimicrobial material may take the form of foam (for example by extrusion) or shavings or cardboard. Moulds made of the antimicrobial material may be prepared into which the food product may be placed. Smaller particles of the material, such as the shavings, may be used to fill the gaps between the individual food products. The food product which may be packaged with the material of the sixth aspect may be a fruit (e.g. nectarines, peaches, apples and pears) or vegetable. Fruit is used herein as an example of produce that is highly susceptible to post-harvest diseases, but other agricultural products such as potatoes, carrots, lettuce etc, could benefit from being protected by the materials derived from this invention.

The inventors also envisage using the antimicrobial wood-derived or bark-derived material according to the second aspect for forming a receptacle or container.

Hence, in a seventh aspect, there is provided a container comprising the antimicrobial material according to the second aspect.

The container may be capable of storing food, i.e. a food container. The container may be capable of storing any food material which may be prone to rotting, wastage or microbial infection, such as fresh food or produce. For example, the food may comprise fruit or vegetables. The antimicrobial material according to the second aspect may also be used for forming receptacles for waste material, or as an additive to waste material containers. Hence, the container according to the seventh aspect may be capable of containing waste, i.e. a waste container. The container may be used to store any potentially degradable waste material, such as food waste. Degradable waste, such as organic kitchen waste, attracts flies and generates bad odours when not treated properly. Hence, the waste container may be a household or commercial waste bin which results in the reduction or elimination of flies or odour.

The antimicrobial material of the second aspect may alternatively be used as an additive to the container. For example, the material may be provided as particles, shavings or powder, a layer of which may be placed into the base of the container, or attached to sides thereof, for exerting its antimicrobial properties on anything that may be introduced into the container. To obtain good results, the antimicrobial materials may be mixed thoroughly with the waste to achieve good contact with the waste and obtain maximal antiseptic effects.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1 shows a chemical reaction scheme showing the conversion of uric acid to urea;

FIG. 2 shows a chemical reaction scheme showing the conversion of urea to ammonia;

FIG. 3 shows a chemical reaction scheme showing the conversion of ammonia and water into ammonium ions;

FIG. 4*a* shows intensively reared broiler chickens in a hen-house;

FIG. 4*b* shows hock burns on the feet of chickens caused by caustic conditions in the hen-house;

EXAMPLES

The inventor set out to devise a method for stimulating antimicrobial properties in plant material comprising cellulose, hemi-cellulose and lignin. Therefore, the inventor:—
1) tested a range of plant-based materials (i.e. pine bark, pine shavings and filter paper), which were heated for different periods of time at different temperatures for their ability to inhibit *Salmonella* spp.;

2) optimised the ability of heated pine shavings (different temperatures and different heating times) to prevent the formation of ammonia under conditions that were optimal for microbial activity (25° C., 30-50% moisture content, 1-5 g uric acid per system, spiked with spent chicken litter each containing 50 g shavings); and 3) tested the effect of dry storage of the treated material on antimicrobial activity.

Example 1

Effect of Heating of Different Source Materials on the Survival of Pathogens Associated with Chicken Litter Different source materials such as Pine bark, Pine wood (*Pinus sylvestris*), and filter paper (made of cellulose) were exposed to a range of temperatures and their antimicrobial effect was assessed against *Salmonella enterica*.

Materials and Methods

The different source materials were initially ground into a course powder and wrapped in several layers of aluminium foil. Subsequently, the material was placed in a muffle furnace and heated to the required temperature for at least 1 hour. After the heated material had been allowed to cool, it was split into three batches, each weighing 1 g. Each batch was placed in a sterile Universal bottle and wetted with 1 ml of a suspension of *Salmonella enterica* containing approximately $10^7$ cfu $ml^{-1}$. Care was taken that the suspension was completely absorbed by the test material.

After incubation for 24 h at 30° C., the material in the bottle was suspended in 9 ml of 0.25 strength Ringer's solution, providing an isotonic diluent. A 10 fold dilution series was prepared, and each dilution was plated onto XLD agar (Xylose lysine deoxycholate agar; Oxoid). Plates were incubated for 36 hours at 37° C. before the *Salmonella* colonies were counted and survival rate calculated.

Results

The results are shown in Tables 1 to 4.

TABLE 1

Effect of different heating temperature on the survival of *Salmonella enterica* (log cfu $g^{-1}$) in ground pine bark (n = 3). Different letters signify significant differences (P < 0.05) between means

| Temperature (° C.) | Survival (log cfu $g^{-1}$ ± SD) | Significance (P < 0.05) |
|---|---|---|
| 50 | 6.30 ± 0.04 | a |
| 100 | 4.29 ± 0.04 | b |
| 150 | 0.00 ± 0.00 | c |
| 200 | 0.00 ± 0.00 | c |
| Significance | P < 0.001 | |

As shown in Table 1, the survival rate of bacteria decreased with increasing temperature. None of the bacteria survived following exposure to pine bark that had been heated at 150° C. or 200° C.

TABLE 2

Effect of different heating temperature on the survival of *Salmonella enterica* (log cfu $ml^{-1}$) in filter paper (n = 3). Different letters signify significant differences (P < 0.05) between means

| Temperature (° C.) | Survival (log cfu $g^{-1}$ ± SD) | Significance (P < 0.05) |
|---|---|---|
| 20 | 6.92 ± 0.03 | a |
| 50 | 6.88 ± 0.05 | a |
| 100 | 6.48 ± 0.05 | b |
| 150 | 4.51 ± 0.06 | c |
| 200 | 4.38 ± 0.03 | c |
| Significance | P < 0.001 | |

As shown in Table 2, the survival rate of bacteria decreased with increasing temperature.

TABLE 3

Effect of source material and temperature on the survival of *Salmonella enterica* (log cfu $ml^{-1}$ ± SD), n = 3

| | Temperature (° C.) | | |
|---|---|---|---|
| Source material | 20° C. | 200° C. | Significance |
| Pine shavings | 4.82 ± 0.08 | 0.00 ± 0.00 | <0.001 |
| Significance | NS | P < 0.01 | |

As shown in Table 3, the survival rate of bacteria decreased with increasing temperature. None of the bacteria survived following exposure to pine shavings that had been heated at 200° C.

TABLE 4

Effect of source material and different temperatures on the survival of *Salmonella enterica* (log cfu $ml^{-1}$ ± SD), n = 3

| Source Material | Temperature (° C.) | | | Significance |
|---|---|---|---|---|
| | 20 | 150 | 200 | |
| Filter paper | 6.45 ± 0.07 | 0.00 ± 0.00 | 0.00 ± 0.00 | P < 0.001 |
| Pine shavings | 5.30 ± 0.05 | 0.00 ± 0.00 | 0.00 ± 0.00 | P < 0.001 |
| Significance | P < 0.001 | NS | NS | |

As shown in Table 4, the survival rate of bacteria decreased with increasing temperature. None of the bacteria survived following exposure to filter paper or pine shavings that had been heated at 150° C. or 200° C.

Conclusion

The inventors observed that pine shavings and pine bark, when heated to temperatures above 50° C., inhibited the growth of *Salmonella* that is present outside the wood itself, i.e. antimicrobial properties were induced after heating. Furthermore, it was observed that heating filter paper also generally increased the antimicrobial properties of this material, but to a lesser extent than that observed with wood and bark shavings obtained from pine. The inventors also noticed that higher temperatures appeared to induce more antimicrobial activity.

The observed antimicrobial activity extends to the surface of the wood resulting in micro-organisms being unable to grow even if they are presented with sufficient water and external nutrients for their growth. The heating effect on wood is believed to be different from that resulting from the processes of torrefaction and ratification, in which timbers are resistant to white-rot fungi and other wood-degrading organisms after being heated to temperatures well above 200° C.

Example 2

Effect of Heating of Pine Shavings on Ammonia Production in Chicken Litter

Materials and Methods

In order to create an environment that is highly conducive to microbial activity and thus conversion of uric acid into ammonia, an experiment was conducted in which the material was wetted to 30% water of its water holding capacity, and amended with 2% spent chicken litter to provide a large microbial inoculum and 6% uric acid that could be converted to ammonia by microbes. All treatments were incubated at 25° C. to simulate conditions in which a young chicken is raised for its meat, i.e. a broiler hen.

Pine shavings were wrapped in several layers of aluminium foil and heated in a muffle furnace. The pine shavings were subjected to various treatments, either heated to different temperatures (120° C. or 150° C.) or exposed to the heat for different amounts of time (up to 72 hours). 50 g of each treated test material was then placed in 2.5 l dispo-jars that were fitted with a sampling port for gas analysis. Each treatment was replicated 4 times and samples of gas and material were taken every 3 or 4 days to assess pH, microbial respiration ($CO_2$ evolution) and ammonium concentration in the material (using an ammonium probe).

Results

The results are shown in Tables 5 to 10.

TABLE 5

Effect of heating at 150° C. and 200° C. for one hour on pH in pine shavings over an incubation time of 11 days. Treatments were compared with perlite and dried fresh shavings. (n = 4) Different letters signify significant differences (P < 0.05) between means within each column

| | Incubation time (days) | | |
|---|---|---|---|
| Treatment | 4 days | 7 days | 11 days |
| Perlite | 6.43 ± 0.05$^a$ | 8.33 ± 0.24$^a$ | 9.48 ± 0.01$^a$ |
| Dried pine shavings | 6.68 ± 0.03$^a$ | 6.67 ± 0.08$^b$ | 8.75 ± 0.10$^{ab}$ |
| 150° C. | 4.29 ± 0.03$^b$ | 4.60 ± 0.23$^c$ | 8.27 ± 0.41$^b$ |
| 200° C. | 5.84 ± 0.11$^c$ | 7.27 ± 0.42$^{ab}$ | 9.13 ± 0.02$^{ab}$ |
| Significance | P < 0.001 | P < 0.001 | P < 0.01 |

As shown in Table 5, the pH of the control, perlite, increased steadily with time. The pH of pine shavings that had been simply dried also increased with time. However, the pH values at 7 and 11 days were considerably lower than the corresponding pH values for perlite. The pH values of pine shavings that had been heated at 150° C. for one hour were significantly lower than both the perlite and the dried pine shavings. The pH values of pine shavings that had been heated at 200° C. for one hour were lower than both the perlite.

TABLE 6

Effect of heating at 150° C. and 200° C. for one hour on microbial activity (mg $CO_2$ $h^{-1}$ $kg^{-1}$) in pine shavings after 4 days incubation at 25° C. Treatments were compared with perlite and dried fresh shavings. (n = 4) Different letters signify significant differences (P < 0.05) between means

| Treatment | Respiration (mg $CO_2$ $h^{-1}$ $kg^{-1}$) |
|---|---|
| Perlite | 272 ± 26$^a$ |
| Dried pine shavings | 146 ± 10$^b$ |
| 150° C. | 6.3 ± 3.2$^c$ |
| 200° C. | 103 ± 18$^b$ |
| Significance | P < 0.001 |

As shown in Table 6, heating pine shavings for one hour at 150° C. significantly reduced the amount of bacterial respiration compared to the two controls, i.e. perlite and pine shavings that had been merely dried. Heating pine shavings for one hour at 200° C. also reduced the amount of bacterial respiration compared to the controls, but not to the same extent as heat treatment at 150° C.

TABLE 7

Effect of heating time at 120° C. on pH of pine shavings over an incubation time of 11 days. Treatments were compared with perlite, commercial shavings and dried fresh shavings. (n = 4)

| | Incubation time (days) | | |
|---|---|---|---|
| Treatment | 4 days | 7 days | 11 days |
| Perlite | 8.31 ± 0.05 | 9.11 ± 0.06 | 8.72 ± 0.07 |
| Commercial shavings | 6.14 ± 0.01 | 6.32 ± 0.09 | 8.53 ± 0.05 |
| Dried shavings | 6.15 ± 0.01 | 7.81 ± 0.28 | 8.51 ± 0.12 |
| 1 hour heating | 5.93 ± 0.02 | 5.33 ± 0.35 | 8.03 ± 0.44 |
| 3 hours heating | 5.79 ± 0.02 | 5.20 ± 0.05 | 7.47 ± 0.33 |
| 6 hours heating | 5.97 ± 0.06 | 4.65 ± 0.22 | 7.17 ± 0.33 |
| 24 hours heating | 6.15 ± 0.09 | 4.55 ± 0.12 | 6.65 ± 0.25 |
| 72 hours heating | 5.01 ± 0.04 | 4.13 ± 0.08 | 4.75 ± 0.31 |
| Significance | P < 0.001 | P < 0.001 | P < 0.001 |

Table 7 illustrates the effects of different exposure times to 120° C. on the pH. As can be seen, the pH decreases steadily with increasing exposure time to the heat.

TABLE 8

Effect of heating time at 120° C. on respiration (mg $CO_2$ $kg^{-1}h^{-1}$) in pine shavings over an incubation time of 11 days. Treatments were compared with perlite, commercial shavings and dried fresh shavings. (n = 4)

| | Incubation time (days) | | |
|---|---|---|---|
| Treatment | 4 days | 7 days | 11 days |
| Perlite | 20.6 ± 4.3 | 12.9 ± 0.56 | 31.5 ± 1.9 |
| Commercial shavings | 85.5 ± 2.4 | 107.9 ± 18.8 | 67.5 ± 4.5 |
| Dried shavings | 501.2 ± 105.4 | 115.4 ± 2.7 | 143.7 ± 9.4 |
| 1 hour heating | 52.0 ± 47.5 | 134.2 ± 34.4 | 117.3 ± 11.6 |
| 3 hours heating | 11.3 ± 6.2 | 107.5 ± 25.6 | 105.0 ± 16.6 |
| 6 hours heating | 1.2 ± 1.2 | 157.6 ± 79.1 | 118.8 ± 5.7 |
| 24 hours heating | 4.3 ± 1.8 | 211.1 ± 20.5 | 102.0 ± 11.4 |
| 72 hours heating | 0.0 ± 0.0 | 3.4 ± 1.8 | 76.0 ± 6.3 |
| Significance | P < 0.001 | P < 0.001 | P < 0.001 |

Table 8 illustrates that the amount of bacterial respiration decreases with increasing exposure time to the heat.

TABLE 9

Effect of heating time at 120° C. on ammonium concentration (mg kg$^{-1}$) in pine shavings over an incubation time of 11 days. Treatments were compared with perlite, commercial shavings and dried fresh shavings. (n = 4)

| Treatment | Incubation time (days) | | |
|---|---|---|---|
| | 4 days | 7 days | 11 days |
| Perlite | 1058 ± 75 | 455 ± 24 | 303 ± 17 |
| Commercial shavings | 50 ± 0 | 508 ± 19 | 590 ± 42 |
| Dried shavings | 80 ± 14 | 360 ± 27 | 310 ± 9 |
| 1 hour heating | 80 ± 11 | 133 ± 96 | 315 ± 54 |
| 3 hours heating | 70 ± 7 | 205 ± 152 | 378 ± 75 |
| 6 hours heating | 117 ± 5 | 43 ± 5 | 323 ± 33 |
| 24 hours heating | 132 ± 40 | 75 ± 20 | 275 ± 19 |
| 72 hours heating | 90 ± 6 | 73 ± 10 | 108 ± 49 |
| Significance | P < 0.001 | P < 0.001 | P < 0.001 |

Table 9 generally shows that the amount of ammonium in pine shavings decreases with increasing exposure time to the heat.

TABLE 10

Effect of heating time at 120° C. on pH of the pine wood shavings (n = 3). Different letters signify significant differences (P < 0.05) between means

| Heating time at 120° C. (Hours) | pH ± SE | Significance |
|---|---|---|
| 0 | 4.68 ± 0.09 | a |
| 0.5 | 4.64 ± 0.02 | ab |
| 1 | 4.48 ± 0.02 | b |
| 2 | 4.31 ± 0.07 | c |
| 3 | 4.42 ± 0.08 | b |
| 4 | 4.44 ± 0.05 | b |
| 5 | 4.35 ± 0.04 | cd |
| 6 | 4.35 ± 0.01 | cd |
| 7 | 4.31 ± 0.04 | cd |
| 8 | 4.35 ± 0.01 | cd |
| 24 | 4.21 ± 0.01 | d |
| 30 | 4.22 ± 0.02 | d |
| 48 | 3.80 ± 0.03 | e |
| Significance | P < 0.001 | |

Table 10 shows that the pH of the pine wood shavings steadily decreases with increasing exposure time to the heat. After 24 hours exposure to 120° C., the pH is 4.21, and after 48 hours exposure, the pH has dropped to 3.8.

Conclusion

The inventors have observed that heating the pine shavings for an hour at 200° C. was less effective at enhancing its antimicrobial properties than heating for an hour at 150° C. Furthermore, heating at 120° C. for more than an hour resulted in significant inhibition of microbial activity and ammonia formation. Also, prolonged heating times at 120° C. enhanced the antimicrobial properties of pine shavings, with the best results being obtained with heating times of 48-72 hours.

The inventors therefore believe that they are the first to discover that heat-treated wood derived materials can be used to kill and prevent the growth of micro-organisms that are not involved in the metabolism of the wood itself. The inventors have not yet determined which mechanisms are responsible for the antimicrobial properties in the cellulosic material. However, although they do not wish to be bound by any hypothesis, they believe that it is not the pine oil per se that is responsible for the antiseptic properties that are conferred to the shavings, but the heating process itself, because supplementation of the pine shavings with pine oil did not enhance the antimicrobial properties of the material. For example, the inventors have shown that filter paper becomes antimicrobial after heating despite the fact that there is no pine oil present in filter paper. The method of the invention works surprisingly well with pine shavings and pine bark. However, it will be appreciated that the method can be used with other wood- or bark-derived derived materials, such as those derived from a variety of hardwoods and softwoods.

Example 3

Use of Antimicrobial Pine Bark and Shavings as Animal Bedding

The inventors have tested the efficacy of the antimicrobial pine bark and shavings in a range of different applications. The inventors have used the material as bedding for use in the animal rearing industry. In particular, it was observed that chickens that are reared in a hen-house which used pine bark and shavings that has been heat-treated for 24 hours at 120° C., did not show any signs of ammonia poisoning and did not suffer from caustic burns compared to untreated samples (see also Example 8). Furthermore, the antimicrobial pine bark and shavings were used as bedding for rabbits. The inventor observed that the bedding reduced odours in the rabbit hutch compared to untreated samples (see also Example 8).

Example 4

Use of Pine Shavings to Reduce Spoilage of Fruit by Fungi

The inventors have tested the use of pine shavings as a mulch to prevent soil-borne fungi from infecting fruits. They have also tested the use of the heated pine shavings as a package material for fruits, with the aim of preventing fungal infections, such as infections of *Botrytis cinerea*.

Method 1

The tested materials were pine shavings and wheat straw. Pine shavings were either heated for 48 hours at 120° C. (treated) or dried at 20° C. (non-treated). Wheat straw was not treated. Sterilised loam soil was inoculated with *Botrytis cinerea* by mixing a colonised plug of Potato Dextrose Agar with 100 g of moist soil. 100 g of the inoculated soil was placed in 10 cm diameter glass jars forming a layer of 3 cm soil.

In each experiment, the test material, i.e. pine shavings (treated and non-treated) or wheat straw, was spread over the inoculated soil in the glass jar to form a mulch layer of 1 cm in depth. A glass jar of inoculated soil without any test material was set aside as a control (non-mulched treatment control). 6 to 8 grapes were then placed on top of each of the mulch layers. The experiment for each test material was replicated four times. Each experiment was incubated for a period of 11 days and grapes were monitored daily for infection with *Botrytis*. If any grapes were infected in one experiment, and if infections were also detected in the replicates, the test material would be scored as "positive". After 11 days incubation the percentage of fruits infected with fungus was calculated for each replicate.

Method 2

12-14 grapes were placed in large Petri-dishes (15 cm diameter) surrounded by either straw, non-heated pine wood shavings, or heated pine shavings. As in Method 1, the heated shavings were heated for 48 h at 120° C. To encourage infection with *Botrytis* into each Petri-dish, a Potato Dextrose plug colonised with *Botrytis* was placed at the edge of each Petri-dish. Test materials were moistened with RO water to encourage fungal growth. Subsequently, the Petri-dishes were closed and incubated for 11 days at 25° C., and following this, the percentage of fruits that were infected with fungus was recorded.

Results

TABLE 11

Number of replicates containing fruits infected with *Botrytis* over a period of 11 days. Fruits were either directly placed on soil inoculated with *Botrytis* (Bare soil) or on a 1 cm layer of straw, non-heated pine shavings or heated pine shavings placed on top of the soil that was inoculated with *Botrytis*. Treatments were incubated at 25° C.

| Treatments | Number of days incubation | | | | | | | | |
|---|---|---|---|---|---|---|---|---|---|
| | 1 | 2 | 3 | 4 | 5 | 6 | 7 | 8 | 11 |
| Bare soil | 4 | 4 | 4 | 4 | 4 | 4 | 4 | 4 | 4 |
| Straw | 0 | 0 | 4 | 4 | 4 | 4 | 4 | 4 | 4 |
| Non-heated Pine shavings | 0 | 2 | 3 | 4 | 4 | 4 | 4 | 4 | 4 |
| Heated Pine shavings | 0 | 0 | 0 | 0 | 0 | 0 | 0 | 0 | 4 |

Table 11 shows that heated pine shavings did not produce any fruits that were infected with *Botrytis* until day 11, when four infected fruits appeared.

TABLE 12

Percentage infected fruits after 11 days. Fruits were either directly placed on soil inoculated with *Botrytis* (Bare soil) or on a 1 cm layer of straw, non-heated pine shavings or heated pine shavings placed on top of the soil that was inoculated with *Botrytis*. Treatments were incubated at 25° C. (n = 4)

| Treatment | Average Percentage of fruits infected with *Botrytis* |
|---|---|
| Bare soil | 100 ± 0 |
| Straw | 100 ± 0 |
| Non-heated pine shavings | 100 ± 0 |
| Heated pine shavings | 34.5 ± 11.1 |
| Significance | P < 0.001 |

Table 12 shows that for heated pine shavings only 34.5% of the fruit were infected, which was significantly less that with the other treatments.

TABLE 13

Percentage infected fruits after 11 days. Fruits were either placed in between straw, non-heated pine shavings or heated pine shavings. All treatments were inoculated with *Botrytis* and incubated at 25° C. (n = 4).

| Treatment | Average Percentage of fruits infected with *Botrytis* |
|---|---|
| Straw | 78.5 ± 5.2 |
| Non-heated pine shavings | 75.5 ± 3.8 |
| Heated pine shavings | 0 ± 0.0 |
| Significance | P < 0.001 |

Table 13 shows that 0% of the fruits were infected when they were placed on a layer of heated pine shavings.

Conclusion

From the data, it is clear that heated pine shavings provided significant protection against *Botrytis* infections.

Example 5

A Container Made of Antimicrobial Pine Bark and Shavings

The inventor prepared a container made out of the heat-treated pine shavings. First, the pine shavings were processed into a pulp, and then added to a plastic mould in the shape of the desired container. The pulp was allowed to dry, thereby forming the container, and removed from the mould. The container was used to store fresh fruit (grapes), and it was observed that the grapes were not prone to rotting.

Example 6

Antimicrobial Activity of Different Wood Types after Heating

The aim of this experiment was to determine if induction of antimicrobial activity during heating was a property that was specific to pine wood, or if this property was also associated with a variety of wood types.

Materials and Methods

Shavings derived from three soft woods, pine (*Pinus sylvestris*), Norway Spruce (*Picea abies*) and Red Cedar (*Juniperus virginiana*), and five hardwoods, Beech (*Fagus sylvatica*), Birch (*Betula* spp), Eucalyptus (*Eucalyptus* spp), Oak (*Quercus robur*) and Ash (*Fraxinus* spp), were used in this example. All shavings were prepared from the core wood of mature trees with a trunk diameter of at least 30 cm.

The different shavings were wrapped in several layers of aluminium foil and the material was placed in a muffle furnace and heated for 72 hours at 140° C. Control shavings were dried at room temperature. Subsequently, the shavings from each treatment were split in three batches, each weighing 1 g. Each batch was placed in a sterile Universal bottle and wetted with 1 ml of a milky suspension of *Salmonella enterica* containing approximately 108 cfu ml$^{-1}$. Care was taken that the suspension was completely absorbed by the test material.

After incubation for 24 h at 30° C., the material in the bottle was suspended in 9 ml of 0.25 strength Ringer's solution and a 10 fold dilution series was prepared that was plated onto XLD agar (Xylose lysine deoxycholate agar; Oxoid). Plates were incubated for 36 hours at 37° C. before the characteristic *Salmonella* colonies were counted and survival calculated.

Results

The results are shown in Table 14.

TABLE 14

Effect of heating at 140° C. for 72 hours of wood shavings derived from 8 tree species on the survival of *Salmonella enterica*. Approximately 108 bacteria were inoculated onto each 1 g batch of shavings and incubated for 36 hours before survival was assessed (n = 3). Different letters signify significant differences (P < 0.05) between means.

| Wood type | Non-Heated | Heated | Significance |
|---|---|---|---|
| Pine | 6.88 ± 0.11$^c$ | 0 | *** |
| Spruce | 7.56 ± 0.06$^d$ | 4.50 ± 0.02 | *** |
| Red Cedar | 5.24 ± 0.07$^b$ | 0 | *** |
| Ash | 7.12 ± 0.06$^c$ | 0 | *** |
| Beech | 6.85 ± 0.19$^c$ | 0 | *** |
| Oak | 7.22 ± 0.13$^c$ | 0 | *** |
| Birch | 7.32 ± 0.04$^{cd}$ | 0 | *** |
| Eucalyptus | 5.93 ± 0.07$^b$ | 5.3 ± 0.06 | *** |
| Significance | *** | *** | |

Table 14 shows that the antimicrobial activity of all tested wood types increased significantly (P<0.001) after heating. Heating of Pine, Red Cedar, Ash, Beech, Oak and Birch at 140° C. for 72 hours resulted in the complete elimination of the inoculated *Salmonella enterica*. Heating of Spruce at 140° C. for 72 hours resulted in a 99.9% reduction (P<0.001) of the inoculated *Salmonella enterica* compared to the control. Heating of *Eucalyptus* at 140° C. for 72 hours had only a small effect of 75% reduction of the inoculated *Salmonella enterica* compared to the control.

Conclusion

It can be concluded that induction of antimicrobial activity during heating is not a property that is specific to only pine wood, since this property is also associated with a variety of other wood types.

Example 7

Effect of Heated Wood Shavings on Fruit Spoilage Caused by *Botrytis cinerea*

The aim of this experiment was to compare the protective effect of treated and non-treated pine shavings against *Botrytis cinerea*.

Materials and Methods

The following test materials were used in this Example:
1. No shavings (control)
2. 0.5 cm layer of non-treated wood shavings
3. 1 cm of non-treated wood shavings
4. 0.5 cm of treated wood shaving
5. 1 cm of treated wood shavings Treatment of the wood shavings meant that the wood shavings were wrapped in several layers of aluminium foil and heated for 72 hours at 140° C. Untreated shavings were dried at room temperature. Sterilised soil was inoculated with colonised culture plates of *Botrytis cinerea* to provide a fungal pathogen source. One culture plate of *Botrytis cinerea* was used for every 500 g of soil. For each experiment, the inoculated soil was placed in 2.5 liter Dispo-safe jars forming a layer that was 5 cm in depth. The test materials were then spread over the inoculated soil, forming the so-called mulch layer. 18 white grapes were placed on top of the soil or mulch layer. Each experiment was replicated 3 times. All jars were incubated at 20° C. for 28 days and the percentage of fruits infected with *Botrytis* was calculated over time.

Results

Figure 5:
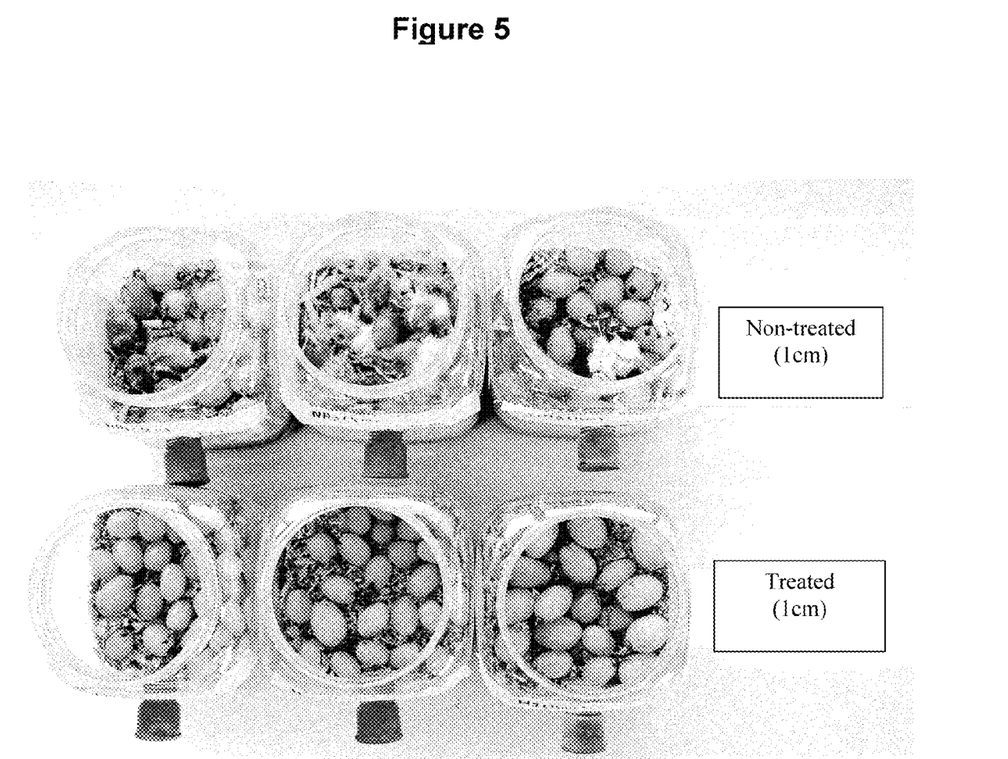
FIG. 5 shows the result of comparing grapes placed on treated and non-treated mulch overlaying soil infected with *Botrytis cinerea* after 28 days incubation at 20° C. Mulch layers were 1 cm thick (n=3)

The results of the effect of heated wood shavings on fruit spoilage caused by *Botrytis cinerea* are illustrated in FIG. 5 and Table 15.

TABLE 15

Percentage (± SEM) grapes infected with *Botrytis* over a period of 28 days when placed on treated mulch or non-treated mulch overlaying a soil inoculated with *Botrytis cinerea*. Mulch layers were either 0.5 cm or 1 cm thick. Controls were placed directly on the soil (n = 3).

| Time (days) | Control | Non-treated 0.5 cm | Treated 0.5 cm | Non-treated 1.0 cm | Treated 1.0 cm |
|---|---|---|---|---|---|
| 0 | 0 | 0 | 0 | 0 | 0 |
| 2 | 8.9 ± 1.1 | 1.1 ± 1.1 | 0 | 3.3 ± 1.9 | 0 |
| 5 | 48.4 ± 2.2 | 27.6 ± 3.0 | 0 | 26.5 ± 3.9 | 0 |
| 12 | 64.9 ± 7.7 | 55.0 ± 6.1 | 7.8 ± 2.2 | 32.0 ± 4.8 | 0 |
| 18 | 100 | 77.3 ± 11.9 | 23.1 ± 3.3 | 51.7 ± 8.8 | 0 |
| 24 | 100 | 79.5 ± 10.9 | 26.5 ± 3.9 | 70.6 ± 2.0 | 0 |

Both Table 15 and FIG. 5 show that treatment of a 1 cm layer of wood shavings resulted in complete protection of grapes from *Botrytis cinerea* over a period of 28 days. Table 15 also shows that treatment of a 0.5 cm layer of wood shavings gave significant protection against *Botrytis cinerea* compared with non-treated mulches. Non-treated shavings provided limited protection against *Botrytis cinerea*.

Conclusion

Treated pine shavings gave significant protection against *Botrytis cinerea* compared with non-treated pine shavings.

Example 8

Effect of Heat-Treated Pine Shavings on the Decomposition of Garbage

The aim of this experiment was to assess the ability of heated pine-shaving to reduce micro-organisms in a garbage receptacle, thus reducing microbial activity and preventing odour formation.

Materials and Methods

The following test materials were used:
10 cm layer of perlite (approximately 152 g),
10 cm layer of non-heated pine shavings (approximately 133 g)
10 cm layer of heated pine shavings (approximately 133 g)

Treated wood shavings were wrapped in several layers of aluminium foil and heated for 72 hours at 140° C. Untreated shavings were dried at room temperature. The different test materials were placed in 2.5 liter Dispo-jars creating a "sorbent" layer. Shredded lettuce and apples (approximately 667 g) were spread on top of the test materials forming a layer that was 10 cm in depth. The jars were incubated at 25° C. for 4 days. Each experiment was replicated three times. The garbage layer and the sorbent layer were assessed every 12 hours for: (1) smell using a subjective scale from 1 to 5 (1=no smell; 5=extremely smelly), (2) ammonium concentration and (3) microbial activity.

Results

Effect on Smell

Figure 6:
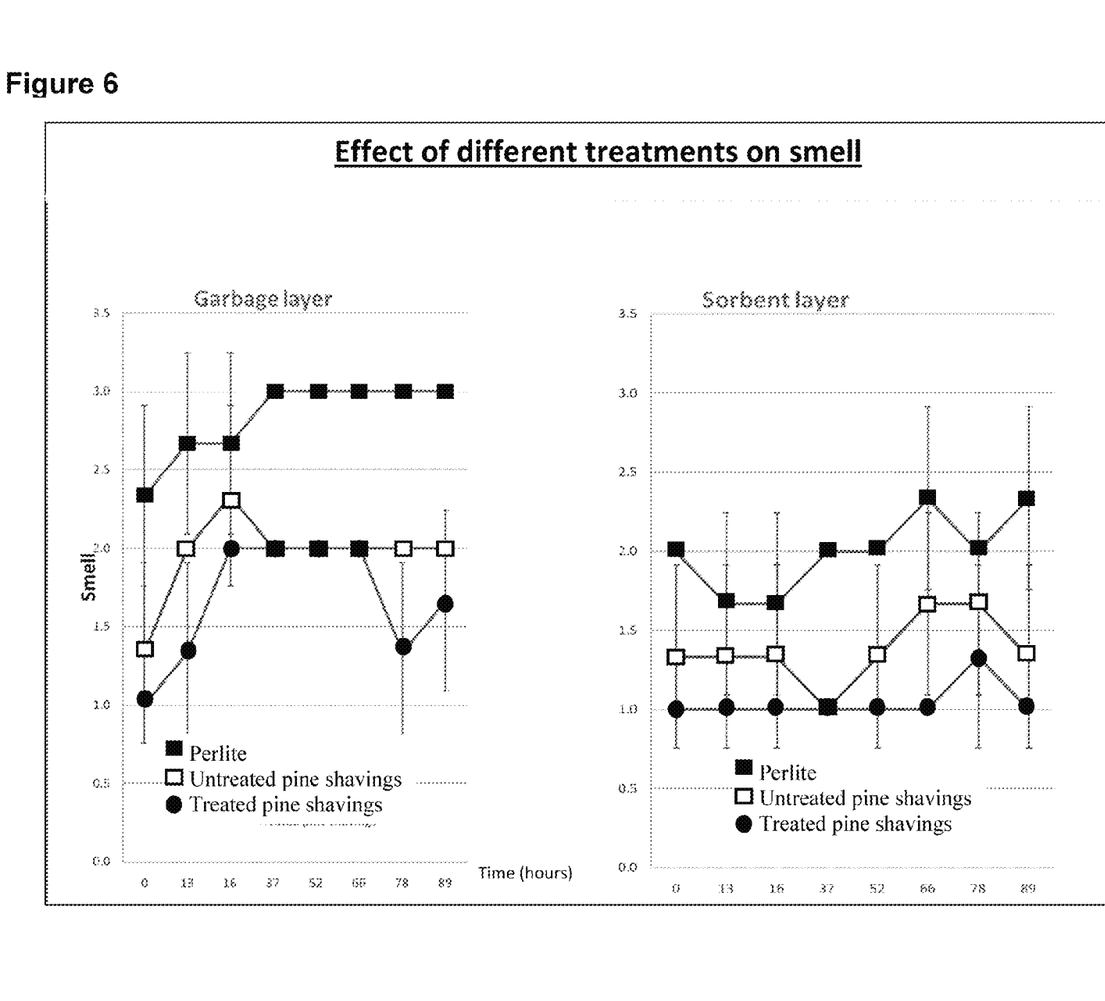
FIG. 6 shows the effect of perlite, non-heated and heated pine shavings on smell. Error bars represent standard error of mean (n=3)

The results of the effect of different treatments of pine shavings on smell are illustrated in FIG. 6. FIG. 6 shows that garbage placed on top of a layer of heated shavings was much less smelly than garbage placed on top of a layer of perlite, and also less smelly than garbage placed on non-heated shavings. The same was true for the smell of the sorbent layer underneath the garbage layer.

A two way ANOVA test was used, showing a significant difference in results (P<0.015). The Turkey HSD multiple comparison test showed significant differences between the different layers (garbage and sorbent) between the perlite, garbage, treated and non-treated pine shavings (P<0.018).

Effect on Ammonium Concentration

Figure 7:
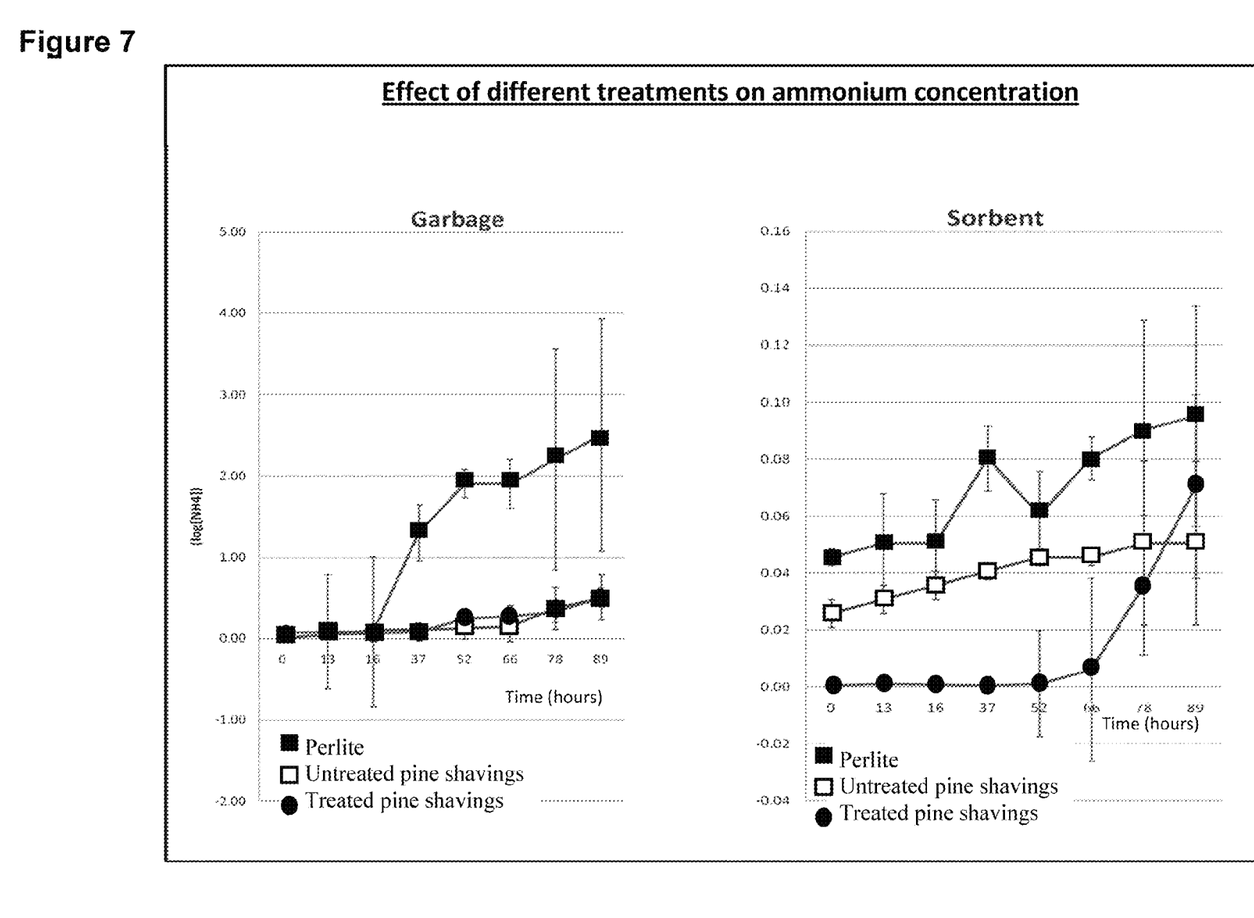
FIG. 7 shows the effect of perlite, non-heated and heated pine shavings on ammonium concentration. Error bars represent standard error of mean (n=3)

FIG. 7 shows the effect of the different treatments of pine shavings on ammonium concentration, which is a measure of microbial activity. As can be seen in the Figure, the ammonium concentration increased over time for perlite, treated and untreated samples. However, the inventors were surprised to see that the ammonium concentrations in the treated pine shavings of the sorbent sample were significantly lower than for the untreated pine shavings and perlite at least for the initial 78 hours of the test.

The different treatments of pine shavings were compared using a multivariate analysis of variance showing a significant difference (Wilks' lambda; P=0.000). A Turkey HSD multiple comparison test was carried out on the different treatments and it has been shown that there was a significant difference between all the different treatments (P<0.025). In comparison between the sorbent and the garbage layer, there was a significant difference between these in all treatments (P=0.000).

Effect on Microbial Activity (Respiration)

Figure 8:
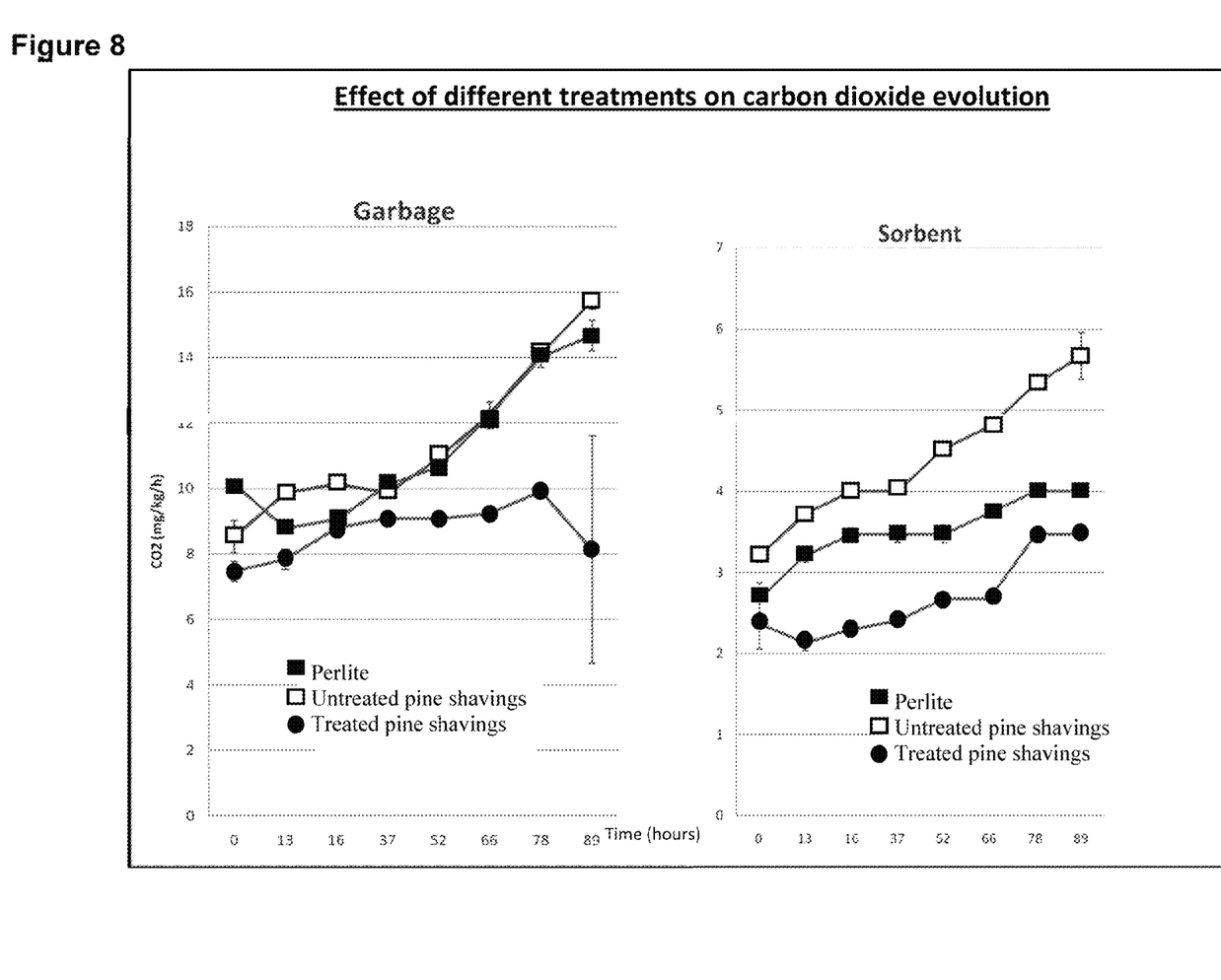
FIG. 8 shows the effect of perlite, non-heated and heated pine shavings on microbial respiration, i.e. carbon dioxide evolution. Error bars represent standard error of mean (n=3).

FIG. 8 shows the effect of the different treatments on carbon dioxide evolution, another measure of microbial activity. FIG. 8 shows that, in general, the amount of carbon dioxide, i.e. microbial activity, increases over time in all the materials tested. The inventors were pleased to observe that the level of carbon dioxide actually decreased for treated pine shavings/garbage) indicated a decrease in microbial activity. Furthermore, in all cases, the level of carbon dioxide was lowest for heat-treated pine shavings.

The different test materials were analysed with a two way ANOVA test and it was found that there was a significant difference between almost all treatments (Wilks' lambda; P=0.000). When compared using a Turkey HSD multiple comparison test there was significant differences between all the different treatments (P=0.000), apart from comparison between perlite and non-treated pine shavings which showed no significant difference (P=0.997) in the garbage layer.

Conclusion

The microbial activity in the garbage layer is reduced by 50% when the garbage is placed over heated pine shavings compared to when to garbage is placed over non-heated pine shavings, or over perlite.

The invention claimed is:

1. A method for preparing antimicrobial material, the method comprising heating precursor material comprising wood or bark or material derived therefrom to a temperature between 110° C. and 200° C. for at least 1.5 hours, wherein the wood or bark is selected from the group consisting of pine (*Pinus* spp), Spruce (*Picea* spp), Cedar (*Juniperus* spp), Beech (*Fagus* spp), Birch (*Betula* spp), Eucalyptus (*Eucalyptus* spp), Oak (*Quercus* spp) and Ash (*Fraxinus* spp).

2. A method according to claim 1, wherein the precursor material is derived from the Pinaceae family.

3. A method according to claim 1, wherein the precursor material is exposed to a temperature of between 110° C. and 175° C.

4. A method according to claim 1, wherein the precursor material is exposed to a temperature of between 110° C. and 150° C.

5. A method according to claim 1, wherein, before the heating step, the method comprises a step of processing the precursor material into small particles.

6. A method according to claim 5, wherein the processing step comprises grinding the precursor material into a powder, or obtaining shavings or preparing a pulp.

7. A method according to claim 1, wherein the precursor material has a mean particle size of less than 2 mm.

8. A method according to claim 1, wherein the method comprises a step of encasing the wood- or bark-derived precursor material in a layer of material, which contains the wood- or bark-derived precursor material as it is exposed to the heat-treatment step.

9. A method of preventing, combating or treating a microbial, bacterial or fungal infection, comprising:
    preparing antimicrobial material according to the method of claim 1;
    applying the antimicrobial material to an environment in which the microbial, bacterial or fungal infection is to be prevented, combated or treated.

10. The method of claim 2, wherein said *Pinus* genus is *Pinus sylvestris* or *Pinus nigra*.

11. A method according to claim 1, wherein the precursor material is exposed to a temperature of less than 150° C.

12. A method according to claim 1, wherein the precursor material is exposed to the treatment temperature for at least 5 hours.

13. A method according to claim 1, wherein the precursor material is exposed to the treatment temperature for at least 24 hours.

14. A method according to claim 1, wherein the precursor material has a mean particle size of less than 1 mm.

15. A method according to claim 1, wherein the precursor material has a mean particle size of less than 0.5 mm.

16. A method according to claim 9, wherein the environment is selected from the group consisting of an animal's bedding, soil where plants are grown, food packaging, and a receptacle or container.

* * * * *